US011849925B1

(12) United States Patent
Aghdam (10) Patent No.: US 11,849,925 B1
(45) Date of Patent: Dec. 26, 2023

(54) VAGINA PROBE WITH BRUSH (71) Applicant: Lida Aghdam, Colleyville, TX (US)

(72) Inventor: Lida Aghdam, Colleyville, TX (US)

( * ) Notice: Subject to any disclaimer, the term of this patent is extended or adjusted under 35 U.S.C. 154(b) by 0 days.

(21) Appl. No.: 17/679,771

(22) Filed: Feb. 24, 2022

Related U.S. Application Data (63) Continuation of application No. 15/488,502, filed on Apr. 16, 2017, now Pat. No. 11,259,785.

(60) Provisional application No. 62/395,934, filed on Sep. 16, 2016.

(51) Int. Cl.
*A61B 10/02* (2006.01)
*A61B 10/00* (2006.01)
*G01N 33/483* (2006.01)
*A61B 5/00* (2006.01)
*G16H 10/40* (2018.01)

(52) U.S. Cl.
CPC ............ *A61B 10/02* (2013.01); *A61B 5/4337* (2013.01); *A61B 10/0096* (2013.01); *A61B 10/0291* (2013.01); *G01N 33/4833* (2013.01); *A61B 2010/0208* (2013.01); *A61B 2010/0216* (2013.01); *G16H 10/40* (2018.01)

(58) Field of Classification Search
None
See application file for complete search history.

(56) References Cited

U.S. PATENT DOCUMENTS

| | | | | |
|---|---|---|---|---|
| 4,157,709 A | * | 6/1979 | Schuster | ............ A61B 10/0291 600/572 |
| 2004/0260201 A1 | * | 12/2004 | Mueller, Jr. | ........... A61B 10/04 600/569 |
| 2005/0277846 A1 | * | 12/2005 | Chou | ................. A61B 10/0291 600/562 |

* cited by examiner

*Primary Examiner* — Michael R Bloch
(74) *Attorney, Agent, or Firm* — Leavitt Eldredge Law Firm; Richard Eldredge (57) ABSTRACT

A method for taking a cervical or vaginal sample includes providing a sampling probe having a housing with a flange at one end and an internal step ring including a protrude follower tab near the distal end; and a shaft inside the housing with a brush and a handle, the shaft having a solid proximal section, a spirally grooved distal section, a retracting compression spring inside the housing on the spirally grooved distal section, and with the housing protruding follower tab engaging a spiral groove in the spiral groove section of the shaft; inserting the sampling probe into a vaginal canal; pushing on the handle causing the brush to protrude the distal end of the housing, with the housing follower tab engaging the shaft spiral groove, causing the shaft and the brush to rotate and take a sample; and releasing the shaft handle to retract the brush into the housing.

6 Claims, 8 Drawing Sheets

VAGINA PROBE WITH BRUSH

FIELD OF DISCLOSURE

The present disclosure relates to medical collection devices and procedures, and in particular, to medical collection devices and procedures for conducting a Pap smear test.

BACKGROUND OF THE DISCLOSURE

The Papanicolaou test, also called Pap smear, Pap test, cervical smear, or smear test, is a screening test comprising taking samples from cervical cells (or vaginal cells if the patient had hysterectomy and is lacking a cervix) to detect potential premalignant and malignant (cancerous) processes in the cervix (and also vagina in case of hysterectomy) which is located at the upper end of vaginal canal. This process also can be used to detect the cause of the cancer, which is Human Papilloma virus, which is a sexually transmitted virus, as well as other sexually transmitted infections like Gonorrhea, *Chlamydia trachomatis* and *Trichomona vaginalis*, which are the main infections, which if untreated, can cause pelvic inflammatory disease that can cause female infertility. Some types of this virus cause genital warts.

A Pap smear test presently is accomplished by using a cell extraction device such as a Pap smear spatula and Pap smear brush or alternatively by a Pap smear broom. In general, a medical practitioner first inserts a speculum into the woman's vagina, spreading the vagina open, allowing access to the cervix. When using a spatula and a brush, the medical practitioner then collects a sample of the cells from the outer opening of the cervix by scraping it with the spatula. Alternatively the medical practitioner may choose to use a plastic-fronded broom (Pap smear broom) instead of the spatula and brush. The cells are removed from the cervix at the end of vaginal canal (or from vaginal walls, if patient had hysterectomy) and are checked in a laboratory under microscope for abnormalities.

The test is an effective, widely used method for early detection of pre-cancer and cancer cells in cervix (or vagina, if patient had hysterectomy). The test may also detect serious sexually transmitted diseases like Human Papilloma virus, *Neiseria gonorrhea, Chlamydia trachomatis* and *Trichomona vaginalis*. Therefore, the test may detect abnormalities and infections in vagina, cervix and endometrium.

One of the difficulties with present method for conducting a Pap smear test is the use of a speculum for spreading the vagina open. Using a speculum in general is uncomfortable for the patient and may cause pain, and in particular it may prove very painful for young female patients or post-menopausal patients with significant atrophy and dry tissue where Pap smear may break the tissue causing pain and bleeding and a very traumatic experience to them, as well as rape victims who want to stay anonymous and do not want to seek medical care. The discomfort may be to a point where patients may avoid the Pap smear test, which may lead to not detecting the early stage of cancerous processes at a point where the cancer may be effectively treated. Also early detection of common sexually transmitted disease and on time treatment may prevent serious pelvic inflammatory disease and infertility in affected women. Furthermore, use of a speculum and a spatula and a brush or a Pap smear broom with the correct procedure usually requires application of these medical collection devices by a medically trained physician or nurse. In rural areas medical facilities and medical personnel and specialized laboratories may not be readily available. In some instances visiting a gynecologist may not be financially accessible for some patients.

What is needed is a better device and method for conducting a Pap smear.

SUMMARY OF THE DISCLOSURE

To alleviate the discomfort or potential injury and accompanying pain that may be caused by a regular Pap smear exam, and also in order to provide access to a Pap smear test in remote areas where specialist medical providers are not available, and/or provide the option of a private anonymous Pap smear test and follow-on associated lab test, this disclosure details a sampling probe that can be used by a medical provider on a patient or by a patient herself in taking Pap smear test samples where the lab test can be done remotely and/or anonymously.

In one embodiment a sampling probe is disclosed, including a housing and an internal shaft with a brush at a distal end of the shaft and a shaft handle at a proximal end of the shaft. The sampling probe further including a retracting compression spring inside the housing over the shaft keeping the distal end of the shaft and coupled brush inside the housing. The shaft further having a spirally grooved distal section engaged by a follower tab at a distal end of housing, where when the shaft handle is pushed for the brush to protrude out of the housing to take Pap smear samples, with the sampling probe inside a vagina canal, the brush protrude the housing rotating. Following the brush taking the Pap smear sample cells, in absence of pressure on the shaft handle the brush is retracted back inside the housing.

The sampling probe may have different housing configuration including a single housing or a two part housing to be elaborated on, in the detailed description section of this disclosure.

The sampling probe further includes a cap with a preservative liquid that is coupled to the distal end of the housing, whether the one piece housing or a distal section of the two pieces housing, preserving the Pap smear sample to be tested in a lab.

The sampling probe disclosed herein is used for taking vaginal or cervical samples for either Pap smear purposes or sexually transmitted diseases.

In another embodiment a method for taking a cervical or vaginal sample (for patient with hysterectomy) for the purpose of Pap smear or detecting certain sexually transmitted diseases is detailed as using one hand, distally inserting a sampling probe into a vaginal canal. Here the sampling probe comprises a housing, a shaft, inside the housing, with a handle at proximal end of the shaft and a spiral groove at the shafts distal section, and a brush coupled to the distal end of the shaft. The sampling probe further includes a retracting compression spring inside the housing on the distal section of the shaft, with the shafts groove engaging a follower tab at the distal end of the housing. The Pap smear test further includes pushing on the shaft handle, against the retracting compression spring, causing the brush to protrude from the distal end of the housing while rotating, and taking a Pap smear sample, After a sample is taken, the shaft handle is released, causing the retracting compression spring to retract the brush into the housing.

Following the Pap smear test a cap containing preservative liquid is coupled to the distal end of the sampling probe housing to preserve the Pap smear sample to be tested.

When a two sections housing sampling probe is employed for Pap smear, the cap with preservative liquid is coupled to the distal section of the two piece housing, preserving the Pap smear sample for testing.

Another method for preserving the Pap smear sample for lab test includes inserting the sampling probe brush into a vial containing a preservative liquid for preserving the Pap smear sample, then removing the sampling probe brush from the vial, sealing the vial and sending the vial to a lab for testing the Pap smear sample in the preservative liquid.

In yet another embodiment of present disclosure a business method is disclosed. The business method includes providing a sampling probe to a customer for a fee, for taking a Pap smear sample by distally inserting the sampling probe into a vagina canal and taking a Pap smear sample. The sampling probe here includes a housing, an internal shaft with a handle at the shaft's proximal end and a spiral groove at the shaft's distal section engaging a follower tab at the distal end of the housing, a retracting compression spring inside the housing on the spirally grooved distal section of the shaft, and a brush coupled to the distal end of the shaft, where the brush is used to take a Pap smear sample.

The business method further includes receiving a used sampling probe from the customer and testing the Pap smear sample, or arranging for a lab to receive the used sampling probe from the customer for testing the Pap smear sample.

The business method further includes arranging for the Pap smear test results to be provided to the customer by communicating directly with the customer via regular mail, electronic mail or telephone; or providing the test results on a publicly available website where the customer can anonymously find the test results based on a code associated with the specific provided sampling probe that is used by the customer.

BRIEF DESCRIPTION OF THE DRAWINGS

The disclosure can be better understood with reference to the following detailed description taken in conjunction with the accompanying drawings which illustrate disclosed embodiments, but which are not necessarily drawn to scale. Wherever possible, the same reference numbers will be used throughout the drawing(s) and accompanying written description to refer to the same or like part, wherein.

DETAILED DESCRIPTION

Disclosed embodiments will now be described more fully hereinafter with reference to the accompanying drawings, in which some, but not all of the disclosed embodiments are shown. Several different embodiments are provided and should not be construed as limiting the application of the disclosure to the details of construction and arrangement of the components or method of use set forth in the following description or illustrated in the following drawings as to the embodiments set forth herein. Rather, these embodiments are provided so that this disclosure will be thorough and fully convey the scope of the disclosure to those skilled in the art.

The present disclosure describes a sampling probe 100 that is used by a physician on a patient or by a patient herself for examining and taking cell samples from body cavities. In particular the disclosed sampling probe 100 is used for taking cervical samples or vaginal samples for patient with hysterectomy for the purpose of Pap smear or detecting certain sexually transmitted diseases.

In one embodiment, a sampling probe 100 device includes a housing 200 with a proximal 228 end and a distal 226 end. The housing 200 further includes a flange 202 at its proximal 228 end, and an internal step ring 204 including a protruding follower tab 206 toward its distal 226 end.

The sampling probe 100 further includes a shaft 208 inside the housing 200 with a proximal 228 end and a distal 226 end. The shaft 208 includes a brush 242 at its distal 226 end and a handle 210 at its proximal 228 end. The shaft 208 further includes a solid proximal section 212, and a spirally grooved distal section 214, where the housing 200 protruding follower tab 206 engages the spiral groove 218 of the shaft 208. The spirally grooved distal section 214 of the shaft 208 includes a short straight groove 216 at the distal 226 end of the shaft 208 followed by the spiral groove 218 around the shaft 208.

The sampling probe 100 further includes a retracting compression spring 900 inside the housing 200 positioned on the spirally grooved distal section 214 of the shaft 208.

As for the configuration of the shaft 208, the solid proximal section 212 of the shaft 208 has a diameter that is larger than the inner diameter of the housing 200 internal step ring 204, and is smaller than the internal diameter of the housing 200. Furthermore, the distal grooved section 214 of the shaft 208 has a diameter smaller than the inner diameter of the housing 200 internal step ring 204.

As for the positioning of the retracting compression spring 900 inside the housing 200, the proximal 228 end of the retracting compression spring 900 is in contact with the distal 226 end of the solid proximal section 212 of the shaft 208 and the distal 226 end of the retracting compression spring 900 is in contact with the housing 200 internal step ring 204. This positioning of the retracting compression spring 900 forces the shaft 208 in its proximal direction 228, where absent any force on the shaft 208 handle 210, the brush 242 at the distal 226 end of the shaft 208 remains inside the housing 200.

The brush 242 at the distal 226 end of the shaft 208 includes a brush bristles section 222 and a brush base section 220. A threaded stud 700 protrudes out of the brush base section 220 and couples the brush 242 to a threaded blind hole 400 at the distal 226 end of the spirally grooved distal section 214 of the shaft 208. Furthermore, there is an O-ring 224 on the brush base section 220, which is compressed between the outer diameter of the brush base section 220 and the inner diameter of the housing 200.

In another embodiment of the sampling probe 100, a bi-sectional housing 500 comprises a two sections configuration with a short distal section 504 detachably coupled to a long proximal section 502. Here the short distal section 504 has a coupling external thread 508 on its proximal end, and the long proximal section 502 has an internal thread 506 on its distal end, enabling coupling of the short distal section 504 to the long proximal section 502 of the bi-sectional housing 500. In this configuration the long proximal section 502 of the bi-sectional housing 500 includes the internal step ring 204. Furthermore in this configuration when the two bi-sectional housing 500 sections are separated the brush 242 detaches from the shaft 208 and remains in the short distal section 504 of the bi-sectional housing 500.

Furthermore, in the two sections housing 500 embodiment of the sampling probe 100 a cap 234 with an open end, a closed end, and an O-ring 236 at its open end couples to the distal 226 end of the separated short distal section 504 of the bi-sectional housing 500 and is configured to hold a preserving liquid 238 to preserve a sample probed by the sampling probe 100.

As with the first embodiment of a one piece housing 200 sampling probe 100, a cap 234 with an open end, a closed end, and an O-ring 236 at its open end couples to the distal 226 end of the housing 200 and is configured to hold a preserving liquid 238 to preserve a sample probed by the sampling probe 100.

The sampling probe 100 housing 200, and 500, shaft 208, brush base section 220, and cap 234 are made of material comprising plastic, metal, ceramic, glass or a combination thereof. Depending of the material used to make the sampling probe 100 housing 200, and 500, shaft 208, brush base section 220, and cap 234 the manufacturing method comprise, injection molding, machining, casting, other suitable manufacturing methods or a combination thereof. The Brush 242 bristles 222 material comprise plastic bristles, polyester strands, natural material such as animal hair, human hair, cotton, any other suitable strands, or a combination thereof. The section of the brush 242 where the bristles 222 are coupled to, which has a hemispherical dome shape in hemispherical brush 710 and a cylindrical rod shape in the cylindrical bristle 800 may be a soft and elastic material or it may be a hard or plastic material including plastic, metal, ceramic, glass, or other suitable material.

The sampling probe 100 disclosed herein is used for taking vaginal or cervical samples for either Pap smear purposes or sexually transmitted diseases.

Furthermore, the Pap smear sampling from the vagina canal using the sampling probe 100 is accomplished by using one hand for holding the sampling probe 100, inserting the sampling probe 100 distally inside the vagina canal toward cervix, pushing the shaft 208 handle 210 against the retracting compression spring 900, causing the brush 242 to rotationally 230 exit the distal 226 end of the sampling probe 100 housing 200 in a forward movement 232 direction, and releasing the shaft 208 handle 210 retracting the brush 242 into the sampling probe 100 housing 200.

In another embodiment a method for taking a cervical or vaginal sample for patient with hysterectomy for the purpose of Pap smear or detecting certain sexually transmitted diseases, is detailed as distally inserting a sampling probe 100 into a vaginal canal. Here the sampling probe 100 comprise a housing 200 with a distal 226 internal step ring 204 including a protruding follower tab 206, an internal shaft 208 with a handle 210 at the shaft's proximal 228 end and a spiral groove 218 at the shaft's distal 226 section, a retracting compression spring 900 inside the housing 200 on the spirally grooved distal section 214 of the shaft 208, with the housing 200 protruding follower tab 206 engaging the spiral groove 218 of the shaft 208, and a brush 242 coupled to the distal 226 end of the shaft 208. The Pap smear further includes pushing on the shaft 208 handle 210, against the retracting compression spring 900, causing the brush 242 to protrude the distal 226 end of the housing 200, with the housing 200 follower tab 206 engaging the shaft 208 spiral groove 218, causing the shaft 208 and the coupled brush 242 to rotate 230 while moving in a forward direction 232 and take a Pap smear sample. After a sample is taken the shaft 208 handle 210 is released, causing the retracting compression spring 900 to retract the brush 242 into the housing 200.

After the sample is taken a cap 234 is coupled to the distal 226 end of the sampling probe housing 200, with the cap 234 comprising an open end, a closed end, and an O-ring 236 at the cap's open end, and containing a preservative liquid 238 for preserving the Pap smear sample. Then the capped sampling probe 240 is sent to a lab for testing the Pap smear sample on the brush 242.

In this embodiment the brush 242 includes a base 220 at its proximal 228 end and bristles 222 at its distal 226 end, an O-ring 224 at brush's base 220, with the O-ring 224 compressed between the brush's base 220 outer diameter and an internal diameter of the sampling probe 100 housing 200 distal 226 end, where this brush 242 configuration in combination with the cap 234 configuration on the sampling probe 100 contains the Pap smear sample and preservative liquid 238 of the cap 234 from leaking into the proximal 228 end of the sampling probe 100.

When a two sections housing 500 sampling probe 100 is employed for Pap smear, where the sampling probe 100 bi-sectional housing 500 includes a two sections configuration with a short distal section 504 detachably coupled to a long proximal section 502, and the long proximal section 502 includes the internal step ring 204. When the two bi-sectional housing 500 sections are separated the brush 242 remains in the short distal section 504, and the detached short distal section 504 of the sampling probe 100 bi-sectional housing 500 with the brush 242 is capped 600. Here the cap 234 contains the preservative liquid 238 and the caped 600 short distal section 504 end of the bi-sectional housing 500 with the brush 242 is sent to a lab for testing the Pap smear sample on the brush 242.

Another method for preserving the Pap smear sample for lab test includes inserting the sampling probe 100 brush 242 into a vial 1100 containing a preservative liquid 238 for preserving the Pap smear sample, then removing the sampling probe 100 brush 242 from the vial 1100, sealing the vial 1100 and sending the vial 1100 to a lab for testing the Pap smear sample in the preservative liquid 238.

As a method for performing the Pap smear, the holding the sampling probe 100, distally inserting the sampling probe 100 into the vagina canal, pushing on the shaft 208 handle 210 and releasing the shaft 208 handle 210 is done using one hand.

In yet another embodiment of present disclosure a business method is disclosed. The business method includes providing a sampling probe 100 to a customer for a fee, for taking a Pap smear sample by distally inserting the sampling probe 100 into a vaginal canal. The sampling probe 100 here includes a housing 200 with a distal 226 internal step ring 204 including a protruding follower tab 206, an internal shaft 208 with a handle 210 at the shaft's proximal 228 end and a spiral groove 218 at the shaft's distal 226 section, a retracting compression spring 900 inside the housing 200 on the spirally grooved distal section 214 of the shaft 208, with the housing 200 protruding follower tab 206 engaging the spiral groove 218 of the shaft 208, and a brush 242 coupled to the distal 226 end of the shaft 208.

The business method further includes receiving a used sampling probe 100 from the customer and testing the Pap smear sample, or arranging for a lab to receive the used sampling probe 100 from the customer for testing the Pap smear sample.

The business method further includes arranging for the Pap smear test results to be provided to the customer by communicating directly with the customer via regular mail, electronic mail or telephone; or providing the test results on a publicly available website where the customer can anonymously find the test results based on a code associated with the specific provided sampling probe 100 that is used by the customer.

Figure 1:
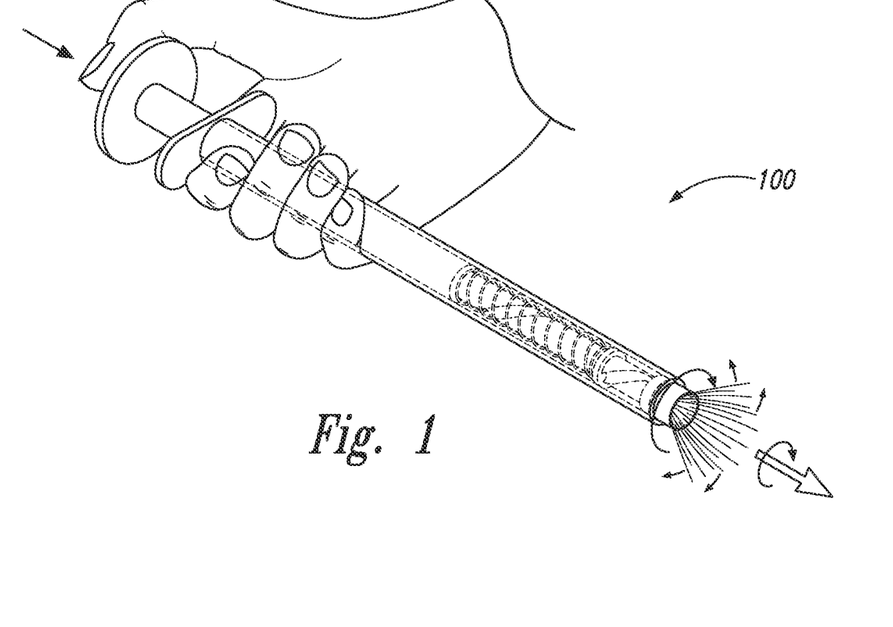
FIG. 1 is an illustration of a sampling probe held with one hand with the shaft handle pushed in and the brush protruding out of the sampling probe housing.

Now referring to the Figures, FIG. 1 is an illustration of a sampling probe 100 held with one hand with a thumb finger on the shaft handle 210 pushing the shaft 208 in the sampling probe 100 housing 200 and the brush 242 protruding out of the sampling probe 100 housing 200. FIG. 1 further illustrate how the brush 242 protrude out of the sampling probe 100 housing 200 while rotating 230, when the shaft handle 210 is pushed distally 226 into the sampling probe 100 housing 200.

Figure 2A:
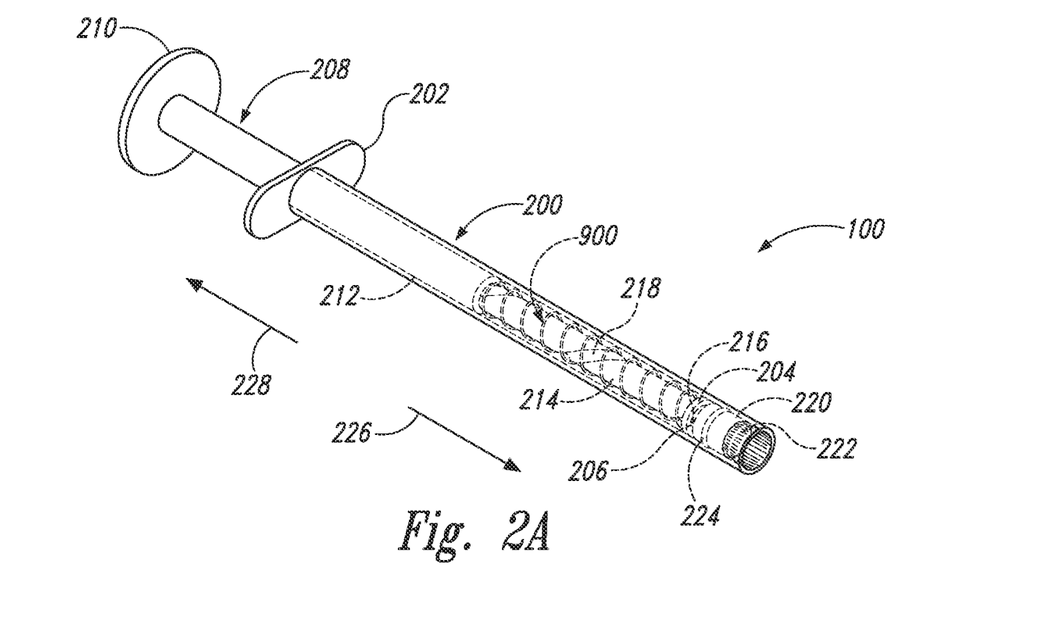
FIG. 2A is an illustration of the sampling probe with the shaft not pushed in and the brush remaining within the sampling probe housing, further showing the shaft handle distal grooved section and retracting compression spring in place.

FIG. 2A shows a sampling probe 100 when there is no force exerted on the shaft handle 210. Here the retracting compression spring 900 is forcing the brush 242 at the distal end 226 of the shaft 208 back in the sampling probe 100 housing 200. A general orientation of distal direction 226 and proximal direction 228 is identified in FIG. 2A, and adhered to throughout this disclosure and balance of the figures. These directional orientations identify the orientation of the sampling probe 100 and all its components as in reference to the orientation that the sampling probe 100 assumes when it is to be used in probing a body cavity (in this disclosure a vagina canal, not shown). The direction towards the body cavity is designated as distal direction 226 and the direction away from the body cavity is designated as proximal direction 228. The same orientation designation carries out throughout this disclosure accordingly for each separate element of the sampling probe 100.

Accordingly, the sampling probe 100 includes a housing 200 with a flange 202 at the housing 200 proximal end 228, The housing 200 further includes an internal step ring 204 and a fixed in place follower tab 206 protruding from and fixed to the internal step ring 204 towards the distal end 226 of the housing 200.

The sampling probe 100 further includes a shaft 208. The shaft 208 resides inside the housing 200. The shaft 208 includes a shaft handle 210 at its proximal end. The shaft 208 is configured having two main sections. The proximal part of the shaft 208 is a solid straight proximal section 212, and the distal 226 section of the shaft is a spirally grooved distal section 214. At the distal 226 end of the shaft, the spiral groove 214 ends in a short straight groove section 216. The outer diameter of the shaft's solid proximal section 212 is larger than the outer diameter of the shaft's spirally grooved distal section 214. Furthermore the outer diameter of the shaft's spirally grooved distal section 214 is smaller than the inner diameter of the housing internal step ring 204. Since the shaft 208 is placed within the housing 200, the outer diameter of the shaft's solid proximal section 212 is smaller than the inner diameter of the housing 200.

Figure 2B:
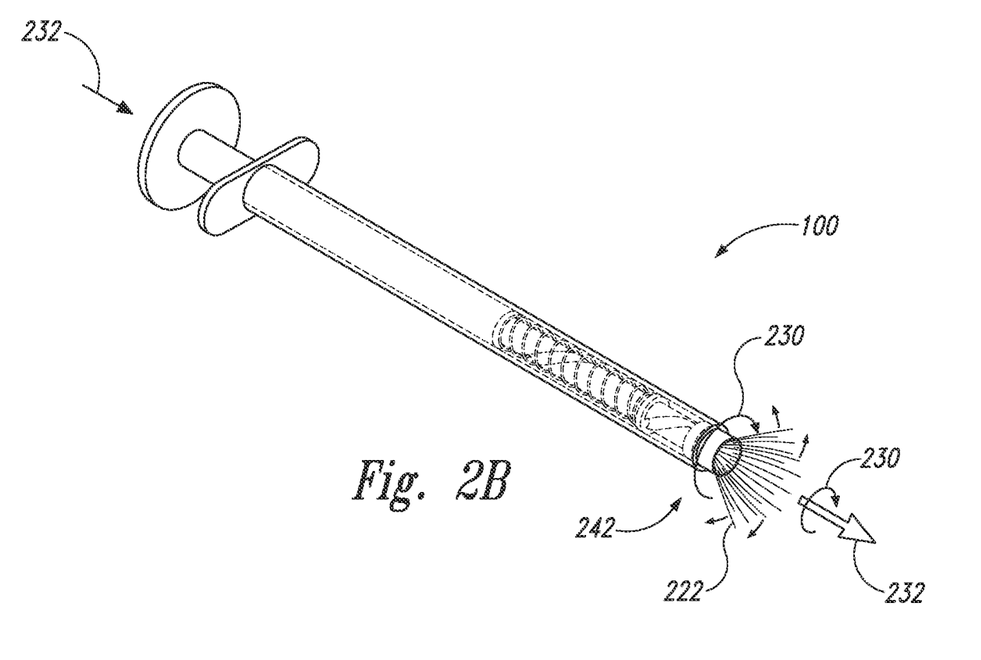
FIG. 2B is an illustration of the sampling probe with the shaft pushed in and the brush protruding out of the sampling probe housing, showing a forward and rotational movement of the brush with the bristles expanding, further showing the shaft handle distal grooved section and retracting compression spring in a compressed configuration.

The sampling probe 100 further includes a brush 242 (refer to FIG. 28) which is coupled to the distal 226 end of the shaft 208. The brush 242 includes a brush base section 220 at its proximal 228 end and a brush bristles section 222 at its distal 226 end. The brush further includes a brush section O-ring 224 on the brush base section 220. With the brush base section 220 of the brush 242 inside the housing 200, the O-ring is compressed between the outer diameter of the brush base section 220 and the inner diameter of the housing 200, preventing passage of any fluid past the brush section O-ring 224 into the housing 200 where the spirally and straight grooved section of shaft 214, 216 is located.

The sampling probe 100 further includes a retracting compression spring 900 positioned on the spirally grooved distal section 214 of shaft 208 inside the housing 200. The retracting compression spring 900 is longitudinally positioned between the distal 226 end of the shaft solid proximal section 212 and the housing internal step ring 204. The retracting compression spring 900 provides a force, pushing on the distal 226 end of the shaft solid proximal section 212 in a proximal direction 228, keeping the brush 242, which is coupled to the distal 226 end of the shaft 208, inside the housing 200. In order to push the brush 242 out of the housing 200, a force opposing the retracting compression spring 900 should be applied to the shaft handle 210, overcoming the expansion force of the retracting compression spring 900 pushing the shaft 208 and the coupled brush 242 in a distal direction 226.

FIG. 2B shows a sampling probe 100, when there is a distal direction 226 force exerted on the shaft handle 210, causing a forward movement 232 of the shaft 208. Here the retracting compression spring 900 is compressed allowing the brush 242 at the distal end 226 of the shaft 208 to protrude out of the distal 226 end of the housing 200 of the sampling probe 100 in a forward movement 232. While the shaft 208 is moving in a distal 226 forward movement 232 direction, the follower tab 206 of the housing 200 initially engages the short straight groove section 216 of the spirally grooved distal section 214 of the shaft and then engages the spiral grooves of the spirally grooved distal section 214 of the shaft, causing the shaft 208 and the coupled brush 242 to move in a rotational movement 230 direction while simultaneously advancing in a forward movement 232. As the brush 242 exits the distal 226 end of the housing 200 the brush bristles section 222, which has been in a contracted formation while inside the housing 200, expands. This forward movement 232 and rotational movement 230, while the brush bristles 222 expand enables contact between the brush bristles 222 and the adjacent walls of the body cavity (here the vagina canal, not shown) when the sampling probe 100 is distally 226 inserted inside the body cavity and the shaft handle 210 is pushed distally 226, to collect cell sample and fluid present in the body cavity for testing.

Figure 2C:
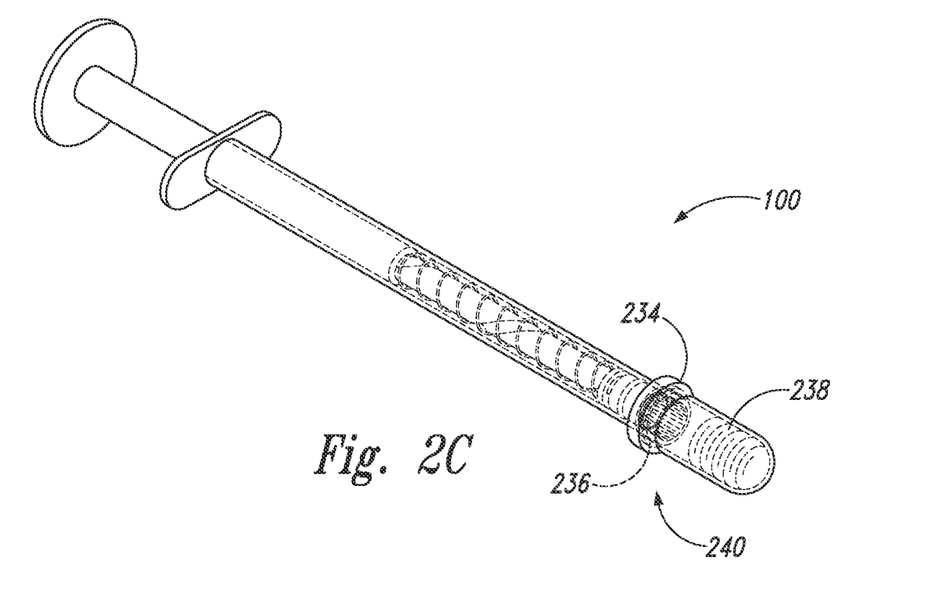
FIG. 2C is an illustration of a used sampling probe with the shaft not pushed in and the brush remaining within the sampling probe housing, and a cap containing preservative liquid capping the distal end of the used sampling probe.

FIG. 2C illustrates a capped sampling probe 240. The capped sampling probe 240 shows a used sampling probe 100 with the brush 242 inside the sampling probe 100 housing 200, with a cap 234 including preservative liquid 238 coupled to the distal 226 end of the sampling probe 100 housing 200. The preservative liquid 238 preserves the samples collected by the brush 242 to be tested later. The cap 234 includes an O-ring 236 at its proximal 228 end. The cap O-ring 236 (with the Cap 234 coupled to the distal 226 end of the sampling probe 100 housing 200) is compressed between the inner diameter of the proximal 228 end of the cap 234 and distal 226 end outer diameter of the sampling probe 100 housing 200. The cap O-ring 236 provides a seal where the sampling probe 100 housing 200 is coupled to the cap 234 and prevents the preservative liquid 238 from spilling out of the capped sampling probe 100.

Figures 3A, 3B:
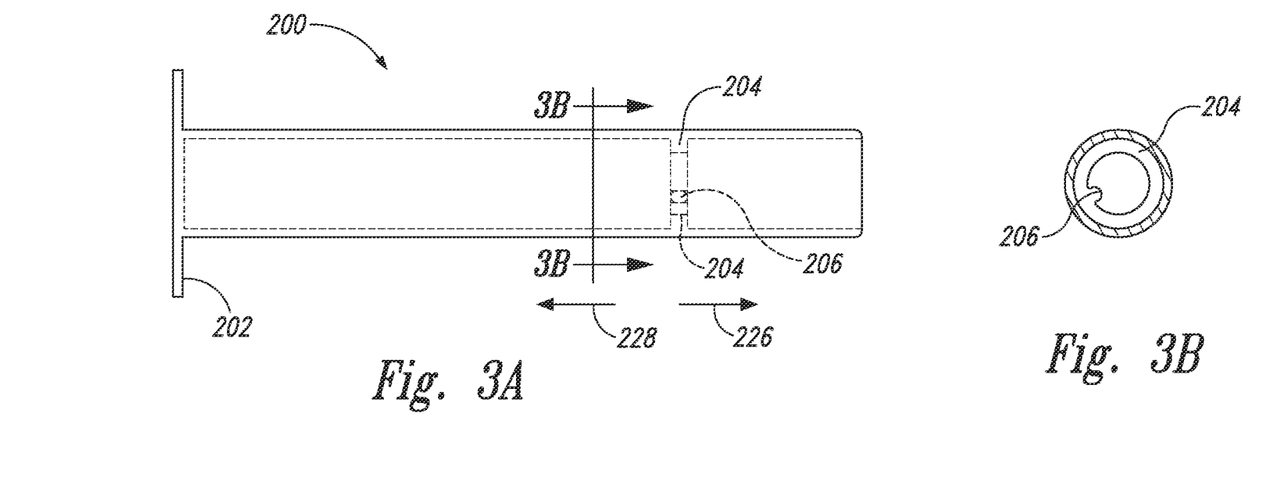
FIG. 3A is an illustration of the sampling probe housing.
FIG. 3B is an illustration of the cross section 3B-3B view of the sampling probe housing.

FIG. 3A shows a standalone housing 200. The distal 226 and proximal 228 orientation of the housing 200 is shown, where the housing 200 includes a flange 202 at its proximal end, and an internal step ring 204 and a fixed in place follower tab 206 protruding radially inward out of the internal step ring 204 towards the distal 226 end of the housing 200.

FIG. 3B details a cross section 3B-3B view of the housing 200, showing the internal step ring 204 and the fixed in place follower tab 206 protrusion of the housing 200.

Figure 4:
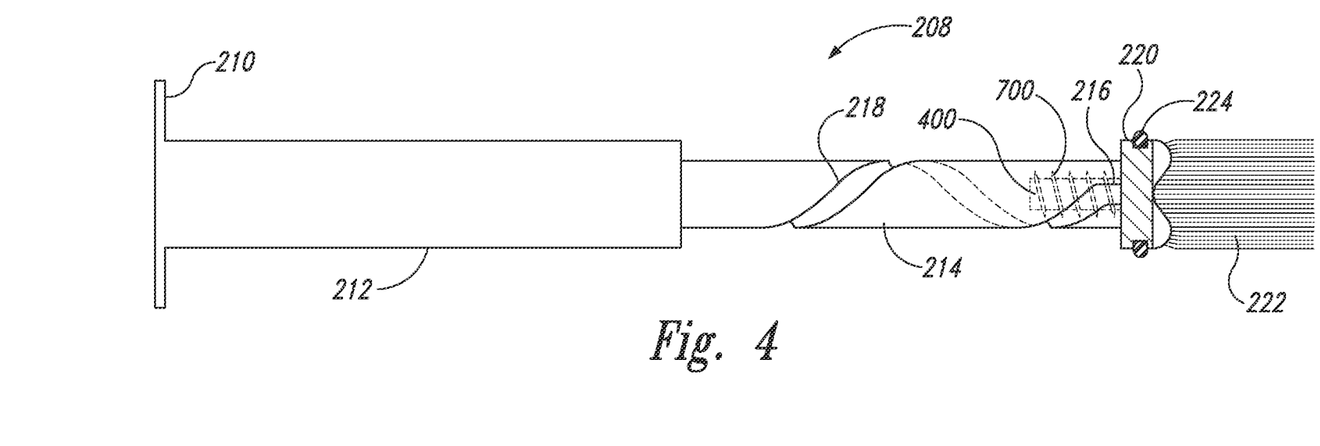
FIG. 4 is an illustration of the sampling probe shaft with the brush coupled to the distal end of the shaft.

FIG. 4 shows a shaft 208 with a coupled brush 242 at its distal 226 end and a shaft handle 210 at its proximal 228 end. The shaft 208 further includes a solid proximal section 212 and a spirally grooved distal section 214. The spirally grooved distal section 214 includes the spiral groove 218 along the spirally grooved distal section 214, and the short straight groove section 216 at the distal 226 end of the spirally grooved distal section 214 of the shaft 208. The shaft 208 further includes a threaded blind hole 400 at its distal 226 end, where the shaft 208 couples to a threaded stud 700 protruding out of the proximal 228 end of the brush 242. FIG. 4 further illustrate a cross sectional view of the brush 242 as coupled to the shaft 208. Brush 242 includes a brush base section 220, a brush bristles section 222, with the bristles 222 in a contracted configuration, and the brush section O-ring 224.

As is illustrated in FIG. 4, the spirally grooved distal section 214 of the shaft 208 has a single groove 218 along the distal grooved section 214 of the shaft 208. This embodiment comprising a single groove, provides for structural integrity and strength of the shaft's 208 spirally grooved distal section 214 through maintaining a substantial cross sectional area of the spirally grooved distal section 214 by only cutting a single groove at each cross section of the diameter of the spirally grooved distal section 214 along the reduced diameter section of the shaft 208 in comparison with the larger diameter of the solid proximal section 212 of the shaft 208.

Figure 5:
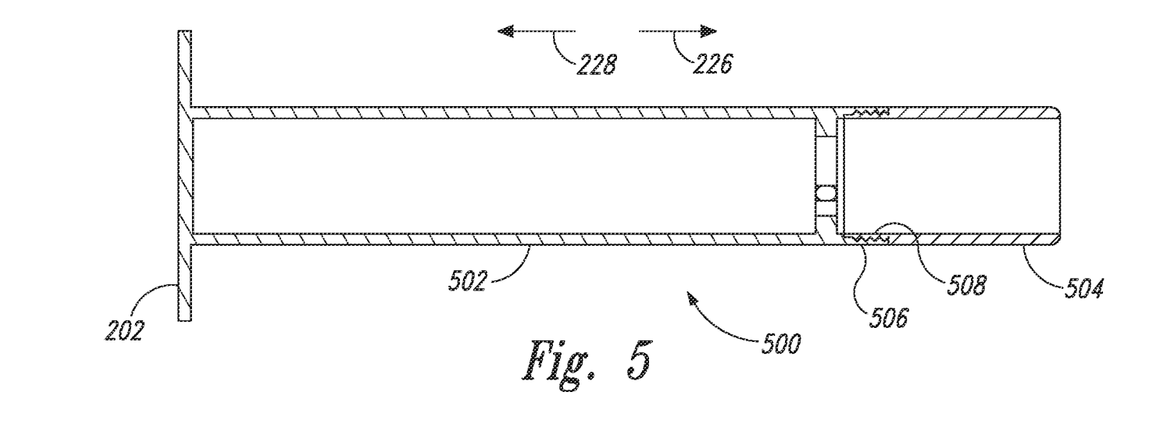
FIG. 5 is an illustration of a two sections housing of a sampling probe.

FIG. 5 shows a bi-sectional housing 500. The bi-sectional housing 500 includes two sections that are coupled to each other forming the bi-sectional housing 500. One of the two sections is a long proximal section 502 of the bi-sectional housing 500 and the other section is a short distal section 504 of the bi-sectional housing 500.

The proximal section 502 of the bi-sectional housing includes the flange 202 on its proximal end and an internal thread 506 at its distal end for coupling to the short distal section 504 of the bi-sectional housing 500. The proximal section of the bi-sectional housing 502 further includes the internal step ring 204 and the protruding from and fixed to the internal step ring 204 follower tab 206 towards its distal end.

The distal section 504 of the bi-sectional housing 500 includes an external thread 508 at its proximal end for coupling to the proximal section 502 of the bi-sectional housing 500. When the external threaded 508 end of the distal section 504 of the bi-sectional housing 500 is screwed into the internal threaded 506 end of the proximal section 502 of the bi-sectional housing 500 the two sections join and form the bi-sectional housing 500 of the sampling probe 100.

In a sampling probe 100 embodiment that uses the bi-sectional housing 500, the brush 242 is located in the distal section 504 of the bi-sectional housing 500. When a bi-sectional housing 500 sampling probe 100 is used for a Pap smear, the sampling probe 100 is distally inserted into the vagina canal and the handle 210 of the shaft 208 of the sampling probe is pushed in, to rotationally protrude the brush 242 out of the bi-sectional housing 500 distal end to collect cell samples. After the cell samples are collected, the shaft handle 210 is released and the retracting compression spring 900 retracts the shaft 208 and the coupled brush 242 back into the bi-sectional housing 500.

Figure 6A:
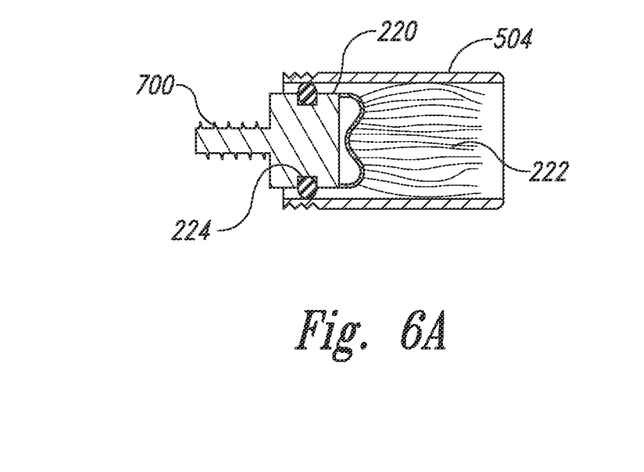
FIG. 6A is an illustration of the decoupled distal section of the sampling probe two sections housing.
Figure 6B:
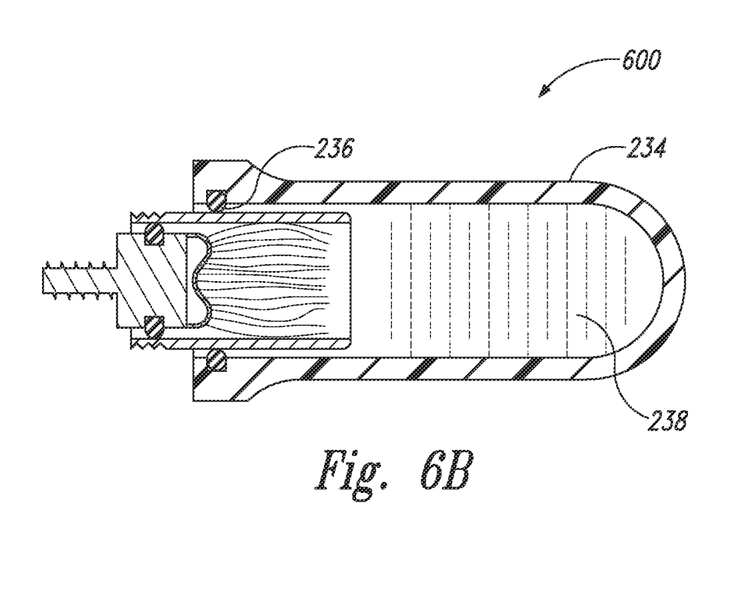
FIG. 6B is an illustration of the capped distal section of the sampling probe two sections housing.

When using the bi-sectional housing 500 sampling probe 100 for Pap smear, when the cell samples are taken and the sampling probe is outside the vagina canal, the distal section 504 of the bi-sectional housing 500 is unscrewed from the proximal section 502 of the bi-sectional housing 500, and the brush 242, as it also decouples and unscrews from the shaft 208, remains in the distal section of the bi-sectional housing 504, as illustrated in FIG. 6A, FIG. 6A shows a standalone distal section of the bi-sectional housing 504 with a brush 242 inside the distal section 504 of the bi-sectional housing 500. The brush 242 includes brush bristles section 222, the brush base section 220 including the threaded stud 700, unscrewed from the shaft 208, and the brush section O-ring 224. In order to preserve the cell samples on the brush bristles 222, a cap 234, which contains preservative liquid 238, is put on the distal end of the distal section 504 of the bi-sectional housing 500 with a brush 242 inside the distal section 504 of the bi-sectional housing 500, as illustrated in FIG. 68.

FIG. 6B illustrates assembly 600 which is a capped distal section 504 of the bi-sectional housing with a brush 242 inside the distal section 504 of the bi-sectional housing 500. FIG. 6B shows a cap 234 with preservative liquid 238 coupled to the distal section 504 of the bi-sectional housing. As shown in FIG. 6B the cap O-ring 236 at the proximal end of the cap 234 is compressed between the inner diameter of the open end of the cap 234 and the outer diameter of the distal section of the bi-sectional housing 504. The cap O-ring 236 seals the gap between the open end of the cap 234 and the distal section 504 of the bi-sectional housing 500, preventing the preservative liquid 238 from spilling from around the external surface of the distal section 504 of the bi-sectional housing. Furthermore the brush section O-ring 224 seals the gap between the brush base section 220 and inside of the distal section 504 of the bi-sectional housing 500, preventing the preservative liquid 238 from spilling from the gap between the brush base section 220 and inside of the distal section 504 of the bi-sectional housing 500. The cap O-ring 236 and the brush base section O-ring 224 provide for a sealed assembly 600 to transfer the cell samples on the brush bristles 222 preserved in preservative liquid 238 to a test facility for testing the Pap smear cell samples.

Figure 7A:
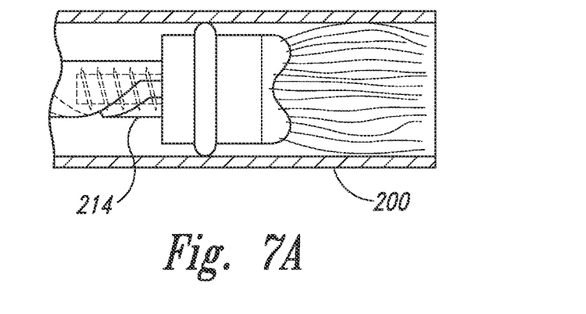
FIG. 7A is an illustration of the brush and its hemispherical bristles inside the sampling probe housing.
Figure 7B:
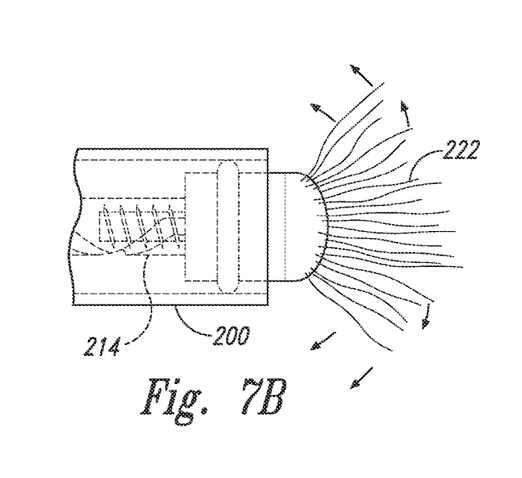
FIG. 7B is an illustration of the brush and its hemispherical bristles outside the sampling probe housing with the bristles in an expanded configuration.
Figure 7C:
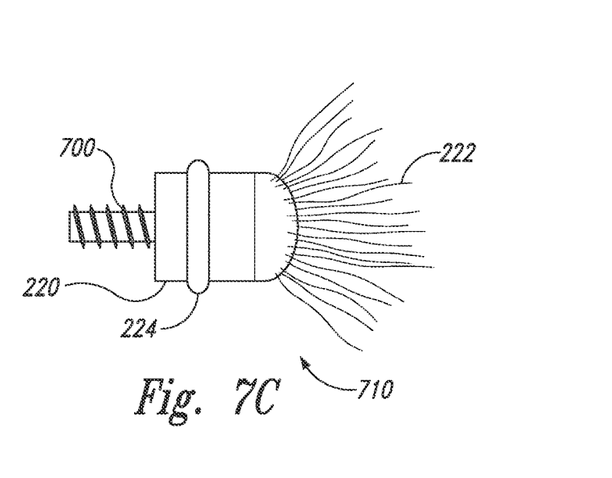
FIG. 7C is an illustration of the brush and its hemispherical bristles by itself.

FIGS. 7A, 7B, and 7C illustrate a hemispherical brush 710 bristle configuration. In FIGS. 7A and 7B the internal step ring 204 is not shown for clarity of illustration. FIG. 7A shows a brush 242 in the housing 200 where the brush is coupled to the grooved 214 end of the shaft 208. In FIG. 7A the brush bristles 222 are inside the housing 200 and maintain a contracted shape. FIG. 7B further shows the brush bristles 222 as expanded when the brush bristles 222 are outside of the housing 200. FIG. 7C illustrates a standalone hemispherical brush 710 with the bristles 222 expanded, the brush base section 220, the brush section O-ring 224 and the threaded stud 700 of the brush at the proximal end 242 of the brush 710.

Figure 8A:
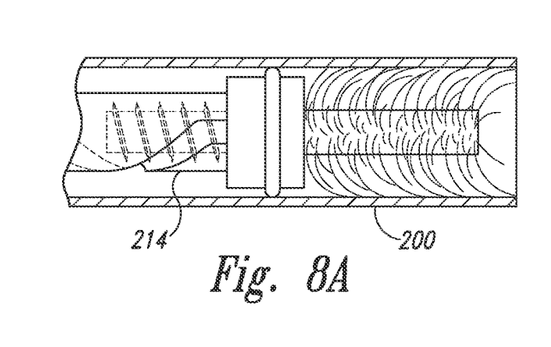
FIG. 8A is an illustration of a brush and its cylindrical bristles inside the sampling probe housing.
Figure 8B:
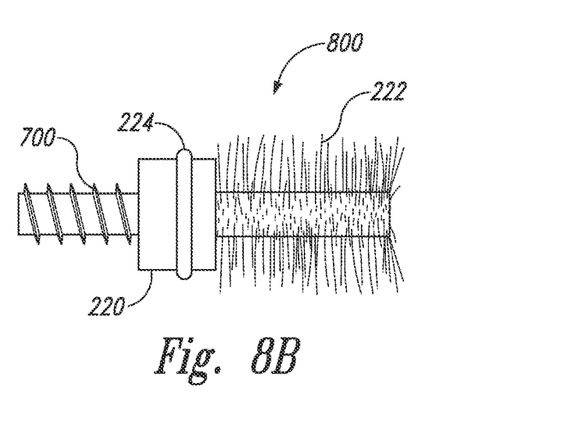
FIG. 8B is an illustration of a brush and its cylindrical bristles outside the sampling probe housing with the bristles expanded radially.

FIGS. 8A and 8B illustrate a cylindrical bristle 800 configuration as an alternative brush bristle 222 configuration shape. In FIG. 8A the internal step ring 204 is not shown for clarity of illustration. FIG. 8A shows a cylindrical bristle 800 configuration brush inside the housing 200 with the bristles in a contracted shape. FIG. 8B further shows a standalone cylindrical bristle 800 configuration brush with the bristles expanded as it would be when the brush is outside the housing 200. FIG. 8B further identifies the brush base section 220, the brush section O-ring 224, and the threaded stud 700 at the proximal end of the brush.

Figure 9:
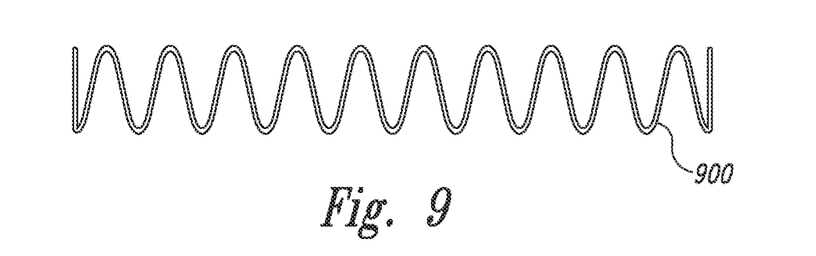
FIG. 9 is an illustration of the retracting compression spring.

FIG. 9 illustrates a standalone retracting compression spring 900.

Figure 10:
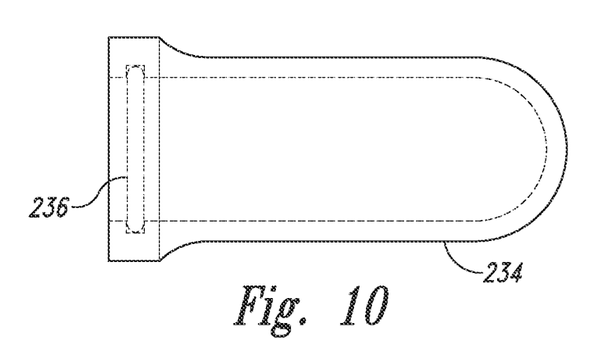
FIG. 10 is an illustration of a cap.

FIG. 10 illustrates a standalone cap 234 and the cap O-ring 236 at the open end of the cap 234.

Figure 11:
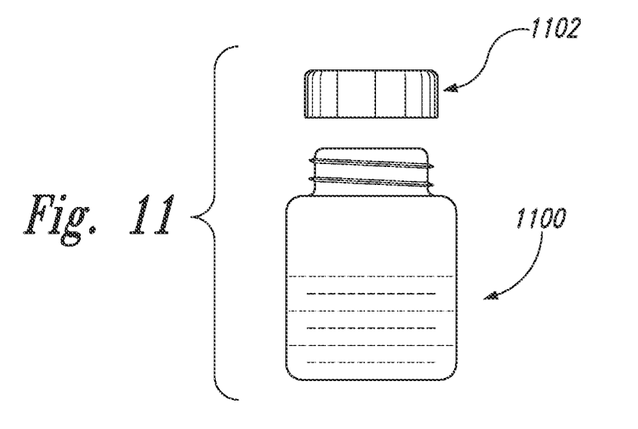
FIG. 11 is an illustration of a vial.

FIG. 11 illustrates a vial 1100 with preservative liquid 238 inside the vial and a vial top 1102. The vial 1100 is an alternative method for capturing or extracting the Pap smear sample cells from the brush 242 bristles 222 after the Pap smear test is done. The cell samples are deposited into the preservative liquid 238 inside the vial 1100 by dipping the brush 242 bristles 222 into the preservative liquid 238 inside the vial 1100 for several times. Once the cell samples are deposited into the liquid preservative 238 inside the vial 1100, then the vial 1100 is sealed using the vial top 1102 and transferred to a lab facility for testing the cell samples.

Figure 12:
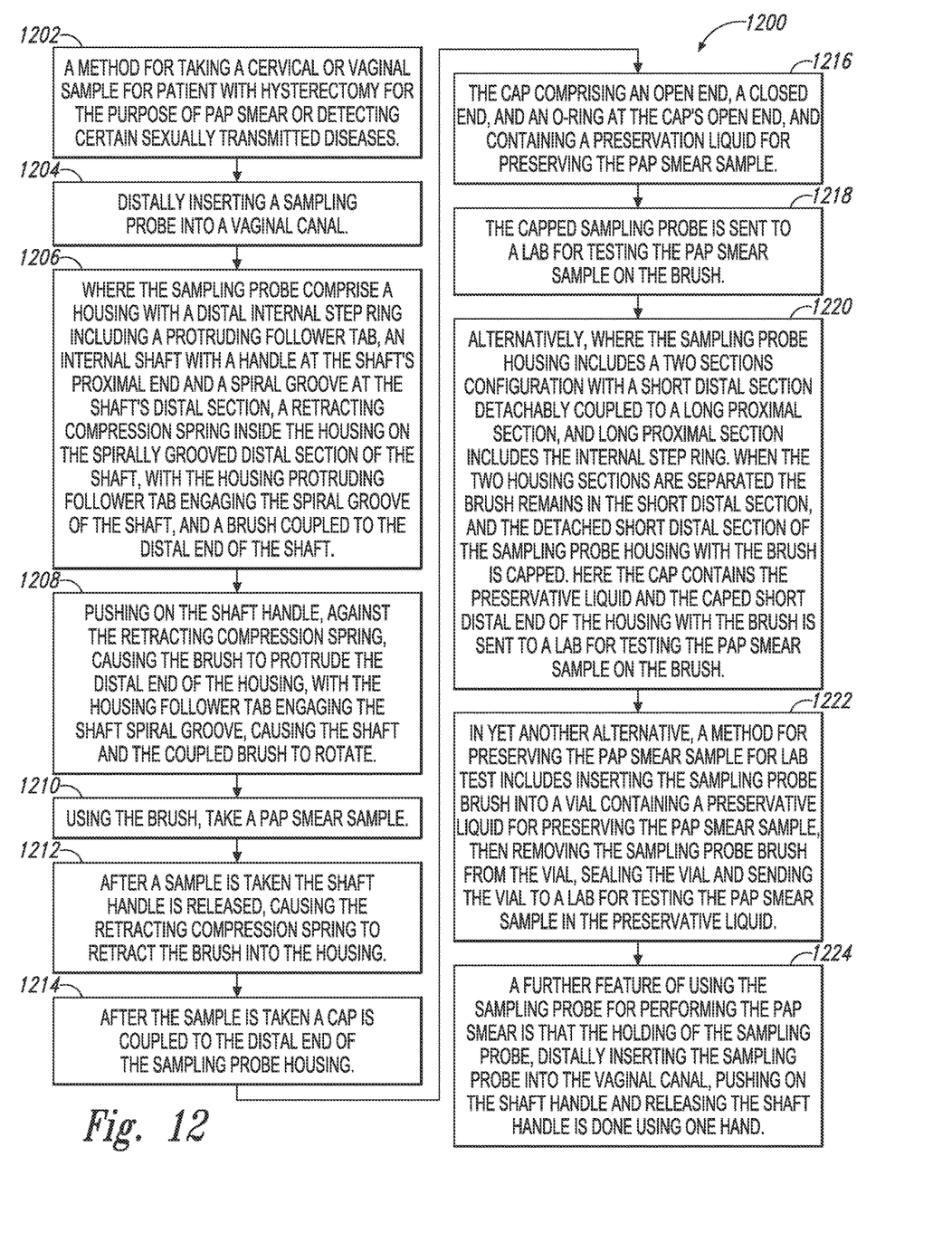
FIG. 12 is a flow chart describing steps involved in method of use of the sampling probe.

FIG. 12 is a flow chart 1200 detailing steps for a method of use of the sampling probe 100 (see FIG. 1) where the method is presented in step 1202 as a method for taking a cervical or vaginal sample for patient with hysterectomy for the purpose of Pap smear or detecting certain sexually transmitted diseases.

This method includes Step 1204 of distally 226 (see FIG. 2A) inserting a sampling probe 100 into a vaginal canal (not shown) (see FIG. 1) and the Step 1206 where the sampling probe 100 comprise a housing 200 with a distal internal step ring 204 including a protruding follower tab 206, an internal shaft 208 with a handle 210 at the shafts proximal 228 (see FIG. 2A) end and a spiral groove 218 at the shafts distal section, a retracting compression spring 900 inside the housing on the spirally grooved distal section 214 of the shaft 208, with the housing protruding follower tab 206 engaging the spiral groove 218 of the shaft 208, and a brush 242 (see FIG. 2B) coupled to the distal 226 end of the shaft 208.

The method includes Step 1208 of pushing on the shaft handle 210 (see FIG. 1) against the retracting compression spring 900, causing the brush 242 to protrude the distal 226 end of the housing 200, With the housing follower tab 206 engaging the shaft spiral groove 218, it causes the shaft 208 and the coupled brush 242 to rotate, and as stated in Step 1210 the brush 242 is used to take a Pap smear sample.

The method further includes Step 1212 where after a sample is taken the shaft handle 210 is released, causing the retracting compression spring 900 to retract the brush 242 into the housing 200. Then Step 1214 follows where after the sample is taken a cap 234 is coupled to the distal 226 end of the sampling probe 100 housing 200 (see FIG. 2C).

Step 1216 in FIG. 12 further elaborate that the cap 234 comprises an open end, a closed end, and an O-ring 236 at the cap's open end (see FIG. 10), and contains a preservative liquid 238 for preserving the Pap smear sample. Step 1218 further provides that the capped sampling probe 240 (see FIG. 2C) is then sent to a lab for testing the Pap smear sample on the brush 242.

Step 1220 of FIG. 12 elaborates on an alternative embodiment, where the sampling probe housing 500 (see FIG. 5) includes a two sections configuration with a short distal section 504 detachably coupled to a long proximal section 502, where the long proximal section 502 includes the internal step ring 204. When the two housing sections are separated the brush 242 remains in the short distal section 504, and the detached short distal section 504 of the sampling probe 100 housing 500 with the brush 242 (see FIG. 6A) is capped 600 (see FIG. 6B). Here the cap 234 contains the preservative liquid 238 and the capped 600 short distal end of the housing with the brush 242 is sent to a lab for testing the Pap smear sample on the brush 242.

Step 1222 provide a further alternative, where a method for preserving the Pap smear sample for lab test includes inserting the sampling probe 100 brush 242 into a vial 1100 (see FIG. 11) containing a preservative liquid 238 for preserving the Pap smear sample, then removing the sampling probe 100 brush 242 from the vial 1100, sealing the vial 1100 and sending the vial 1100 to a lab for testing the Pap smear sample in the preservative liquid 238.

Step 1224 of FIG. 12 further elaborates that a feature of using the sampling probe 100 for performing the Pap smear is that the holding of the sampling probe 100, distally 226 inserting the sampling probe 100 into the vagina canal, pushing on the shaft 208 handle 210 and releasing the shaft 208 handle 210 is done using one hand (see FIG. 1).

Figure 13:
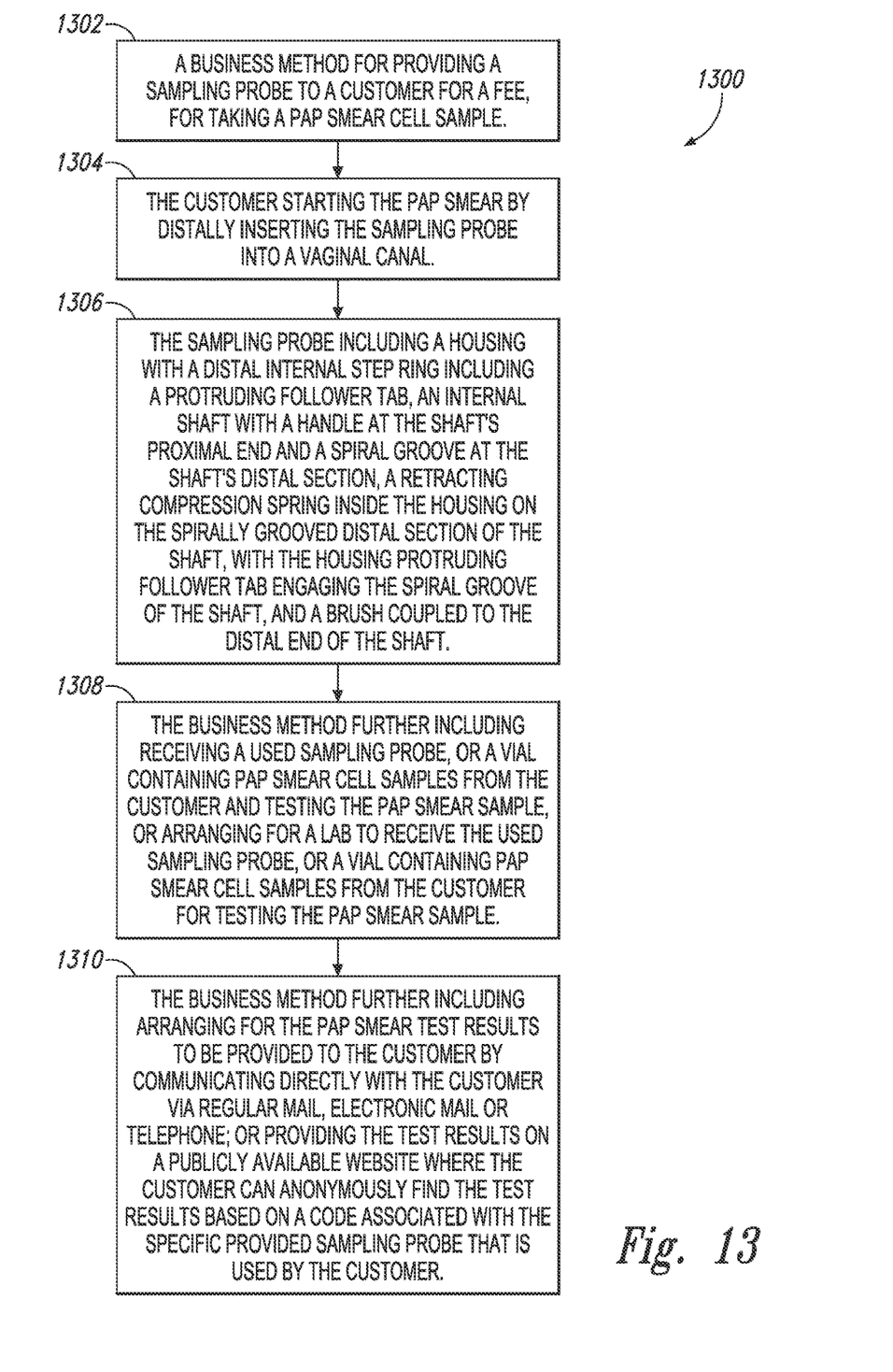
FIG. 13 is a flow chart describing the business method of providing a sampling probe to a customer for taking a Pap smear sample.

FIG. 13 is a flow chart detailing steps for a business method 1300, where the method is presented in step 1302 as a business method for providing a sampling probe 100 (see FIG. 2A) to a customer for a fee, for taking a Pap smear cell sample. Step 1304 further elaborates that after the customer acquire the sampling probe 100, the customer will start the Pap smear by distally inserting (see FIG. 1) the sampling probe 100 into a vaginal canal (not shown).

Step 1306 further elaborates on the configuration of the sampling probe 100 (see FIG. 2) as the sampling probe 100 including a housing 200 with a distal 226 internal step ring 204 including a protruding follower tab 206, an internal shaft 208 with a handle 210 at the shafts proximal end 228 and a spiral groove 218 at the shafts distal section 226, a retracting compression spring 900 (see FIGS. 2 and 9) inside the housing 200 on the spirally grooved distal section 214 of the shaft 208, with the housing protruding follower tab 206 engaging the spiral groove 218 of the shaft, and a brush 242 (see FIG. 2B) coupled to the distal 226 end of the shaft 208.

Step 1308 then details the business method 1300 as the business method 1300 further including receiving a used sampling probe 100, or a vial 1100 containing Pap smear cell samples (see FIGS. 2C, 6B, 11) from the customer and testing the Pap smear sample, or arranging for a lab to receive the used sampling probe 100, or a vial 1100 containing Pap smear cell samples from the customer for testing the Pap smear sample.

As for providing the test results to the customer, Step 1310 details the business method 1300 further, as to including arrangement for the Pap smear test results to be provided to the customer by communicating directly with the customer via regular mail, electronic mail or telephone; or providing the test results on a publicly available website where the customer can anonymously find the test results based on a code associated with the specific provided sampling probe 100 that is used by the customer.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purpose of limitation.

What is claimed is:

1. A method for taking a cervical or vaginal sample for a patient, the method comprising:
    providing a sampling probe having a housing with a proximal end and a distal end, the housing further having a flange at the proximal end and an internal step ring including a protrude follower tab near the distal end of the housing; and a shaft having a proximal shaft end and a distal shaft end, the shaft positioned inside the housing and further comprising a brush at the distal shaft end and a handle at the proximal shaft end, the shaft further comprising a solid proximal section, a spirally grooved distal section, a retracting compression spring inside the housing on the spirally grooved distal section of the shaft, and with the housing protruding follower tab engaging a spiral groove in the spiral groove section of the shaft;
    inserting the provided sampling probe into a vaginal canal;
    pushing on the shaft handle while the provided sampling probe is inserted, against the retracting compression spring, thereby causing the brush to protrude from the distal end of the housing, with the housing protruding follower tab engaging the shaft spiral groove, thereby causing the shaft and the brush to rotate and take a pap smear sample; and
    releasing the shaft handle, causing the retracting compression spring to retract the brush into the housing.

2. The method of claim 1, further comprising:
    removing the provided sampling probe from the vaginal canal;
    coupling a cap to the distal end of the housing after removal, the cap configured to preserve the pap smear sample forming a capped sampling probe; and
    sending the capped sampling probe to a lab for testing.

3. The method of claim 2, wherein the brush further comprises a base at a proximal end and bristles at a distal end, and an O ring positioned between an outer diameter of the base and an inner diameter of the housing, wherein the pap smear sample is contained within the housing between the O ring and the housing distal end after releasing the shaft handle.

4. The method of claim 3, wherein the housing further comprises a short distal section detachably coupled to a long proximal section, wherein the long proximal section comprises the internal step ring such that when the short distal section and the long proximal section are separated, the brush remains in the short distal section.

5. The method of claim 1, further comprising:
    removing the provided sampling probe from the vaginal canal;
    inserting the brush into a vial containing a preserving solution for preserving the pap smear sample after removal;
    removing the brush from the vial; and
    sealing the vial and sending the vial to a lab for testing the pap smear sample.

6. The method of claim 1, wherein the method is performed by a user holding the provided sampling probe, inserting the provided sampling probe into the vaginal canal, pushing on the shaft handle, and releasing the shaft handle using one hand.

\* \* \* \* \*